United States Patent
Erhard et al.

(10) Patent No.: US 10,448,911 B2
(45) Date of Patent: Oct. 22, 2019

(54) METHOD AND DEVICE FOR DISPLAYING MEDICAL IMAGES

(71) Applicant: KONINKLIJKE PHILIPS N.V., Eindhoven (NL)

(72) Inventors: Klaus Erhard, Hamburg (DE); Hanno Heyke Homann, Hannover (DE); Jonas Rikard Rehn, Sollentuna (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 432 days.

(21) Appl. No.: 15/030,450

(22) PCT Filed: Oct. 30, 2014

(86) PCT No.: PCT/EP2014/073271
§ 371 (c)(1),
(2) Date: Apr. 19, 2016

(87) PCT Pub. No.: WO2015/063188
PCT Pub. Date: May 7, 2015

(65) Prior Publication Data
US 2016/0302746 A1    Oct. 20, 2016

(30) Foreign Application Priority Data

Oct. 30, 2013 (EP) .................... 13190869

(51) Int. Cl.
| | | |
|---|---|---|
| *A61B 6/00* | (2006.01) | |
| *A61B 6/02* | (2006.01) | |
| *G06T 11/00* | (2006.01) | |

(52) U.S. Cl.
CPC .............. *A61B 6/466* (2013.01); *A61B 6/025* (2013.01); *A61B 6/4452* (2013.01); *A61B 6/467* (2013.01);

(Continued)

(58) Field of Classification Search
CPC ........ G06T 11/008; A61B 6/025; A61B 6/502
See application file for complete search history.

(56) References Cited

U.S. PATENT DOCUMENTS 7,702,142 B2    4/2010  Ren
7,760,924 B2    7/2010  Ruth
(Continued)

FOREIGN PATENT DOCUMENTS

| DE | 102012203765 | 9/2013 |
| WO | 2006/119426 | 11/2006 |
| WO | 2014/207080 | 12/2014 |

OTHER PUBLICATIONS

Richard, et al., : "Mammogram Registration: A Phantom-Based Evaluation of Compressed Breast Thickness Variation Effects", IEEE Transactions on Medical Imaging, IEEE Service Center, Piscataway, NJ, US, vol. 25, No. 2, Feb. 1, 2006.

(Continued)

*Primary Examiner* — Dani Fox
(74) *Attorney, Agent, or Firm* — Larry Liberchuk (57) ABSTRACT

Medical images are acquired in a tomosynthesis process. Processed 3D volume data representing a target acquired from scanning may be viewed from a set of forward projection directions, in which one or more forward projections through the processed 3D volume data is oblique relative to a central acquisition direction of the scanning process. The first set of forward projections is then displayed as a set of synthetic mammograms. Therefore, a medical practitioner can more easily identify abnormalities within a target volume, because the relative displacement of abnormalities at different depths in the target volume will change at different rates dependent on the viewing angle as the viewing position is moved around the target.

12 Claims, 8 Drawing Sheets

(52) U.S. Cl.
CPC ............ *A61B 6/502* (2013.01); *A61B 6/5223* (2013.01); *G06T 11/008* (2013.01)

(56) References Cited

U.S. PATENT DOCUMENTS

| | | |
|---|---|---|
| 8,044,972 B2 | 10/2011 | Hall |
| 8,923,589 B2 | 12/2014 | Noda |
| 2009/0147073 A1 | 6/2009 | Getty |
| 2012/0127174 A1 | 5/2012 | Naidu |
| 2013/0136333 A1 | 5/2013 | Dennerlein |
| 2013/0177213 A1 | 7/2013 | Lee |
| 2015/0042658 A1 | 2/2015 | Erhard |

OTHER PUBLICATIONS

A. Ardeshir Goshtasby, "2-D and 3-D Image Registration for Medical, Remote Sensing, and Industrial Applications", Wiley Press, 2005.
Gur, et al., "Dose reduction in Digital Breast Tomosynthesis (DBT) Screening using Synthetically Reconstructed Projection Images", Academic Radiology, vol. 19, No. 2., Oct. 3, 2011.

METHOD AND DEVICE FOR DISPLAYING MEDICAL IMAGES

CROSS REFERENCE TO RELATED APPLICATIONS

This application is the U.S. National Phase application under 35 U.S.C. § 371 of International Application No. PCT/EP2014/073271, filed Oct. 30, 2014, published as WO 2015/063188 on May 7, 2015, which claims the benefit of European Patent Application Number 13190869.1 filed Oct. 30, 2013. These applications are hereby incorporated by reference herein.

FIELD OF THE INVENTION

The present invention relates to a method for displaying medical images. In particular, the invention relates to a device for displaying medical images acquired from a target using X-rays. The present invention also relates to a method for displaying medical images acquired from a target using X-rays, to an X-ray imaging system and to a computer program element and a computer-readable medium.

BACKGROUND OF THE INVENTION

Mammogram screening, for example, is an important procedure for the detection and monitoring of breast abnormalities and diseases at an early stage. Medical personnel, such as doctors or radiologists, may detect abnormalities directly from X-ray images. The X-ray tomosynthesis method, for example, is growing in use. X-ray tomosynthesis is a technique for producing 3D image volumes through a target using X-ray systems, although other techniques for providing such 3D volumes are known.

U.S. Pat. No. 8,044,972 discusses a system and a method that visualizes medical data. Tomosynthesis, or information from a CT or C-arm system, enables the viewing of slices through a computed 3D volume of a breast. However, interpreting information provided from the tomosynthesis data is a challenging task, because not all information is clearly visible.

U.S. Pat. No. 7,760,924 discusses a system capable of displaying a conventional mammogram alongside a view derived from tomosynthesis projection images.

SUMMARY OF THE INVENTION

There may thus be a need to provide enhanced viewing modalities of a patient that enable an improved assessment of disease development.

The object of the present invention is solved by the subject-matter of the independent claims, wherein further embodiments are incorporated in the dependent claims. It should be noted that the following described aspects of the invention apply also for the device for displaying medical images, for the method for displaying medical images acquired from a target using tomosynthesis, for the X-ray imaging system, for the computer program element, and for the computer-readable medium.

According to the present invention, a device for displaying medical images acquired from a target using tomosynthesis is provided. The device comprises the following features:
an interface unit,
a processing unit, and
a display unit.

The interface unit is configured to provide processed 3D volume data representing a target, computed from a plurality of X-ray images through the target acquired along a plurality of acquisition directions. The interface unit is configured to input a prior mammogram image. The processing unit is configured to compute a first set of forward projections in one or more projection directions through the target as represented by the processed 3D volume data, wherein at least one of the projection directions is oblique relative to the central acquisition direction. The processing unit is configured to compute an optimal forward projection angle through the 3D volume data, which matches the projection angle of the prior mammogram image. The display unit is configured to display the first set of forward projections as a corresponding first set of synthetic mammograms beginning from the computed optimal forward projection angle through the 3D volume data.

The viewing of synthetic mammograms in oblique directions enables the presentation of the 3D tomosynthesis data in one or more views of a set of synthetic 2D mammograms as a first overview of the patient data, for example. This aids a radiologist in more effectively searching the 3D volume.

The use of a projection direction, which can be oblique, enables a radiologist to benefit from a range of potential views of the 3D data set, rather than using a view from a single, central projection only.

It will be appreciated that the term "processed 3D volume data" refers to the output of a tomosynthesis imaging process, where a detector acquires a number of X-ray images taken through a target. The images are taken from different X-ray source angles. A post-processing operation, for example using a shift-and-add process, is used to provide the processed 3D volume data representing the target.

According to the invention, a method for displaying medical images acquired from a target using tomosynthesis is also provided. The method comprises the following steps:
a) providing processed 3D volume data representing a target, computed from a plurality of X-ray images through the target acquired along a plurality of acquisition directions;
a1) providing a prior mammogram image;
a2) computing an optimal forward projection angle through the 3D volume data which matches the projection angle of the prior mammogram image;
b) computing a first set of forward projections in one or more projection directions through the target as represented by the processed 3D volume data, wherein at least one of the projection directions is oblique relative to a central acquisition direction;
c) displaying the first set of forward projections as a corresponding first set of synthetic mammograms beginning from the computed optimal forward projection angle through the 3D volume data.

According to the invention, an X-ray imaging system is also provided wherein the X-ray imaging system comprises:
an X-ray image acquisition arrangement; and
a display arrangement;
The display arrangement is provided as a device according to one of the above-mentioned examples.

According to the invention, a computer program element for controlling a device for displaying medical images acquired from a target using tomosynthesis is also provided, which, when being executed by a processing unit, is adapted to perform the method steps as discussed in the example above.

According to the invention, a computer-readable medium having stored the program element described in the previous example is provided.

According to an aspect of the invention, it is proposed to compute synthetic mammograms in oblique directions, which are typically chosen between the start and the end angle of a tomosynthesis projection sequence, but are not restricted to the angles of the tomosynthesis projection sequence. The resulting oblique synthetic mammograms may, for example, then be displayed on display means, for example a monitor or polarization glasses for 3D stereoscopy.

The viewing of synthetic mammograms in oblique directions enables the presentation of the 3D tomosynthesis data in one or more views of a series of synthetic 2D mammograms, for example as a first overview of the patient data. Hence, oblique synthetic mammograms support the radiologist in optimizing the workflow for reading a volumetric 3D tomosynthesis data set. Furthermore, a more accurate verification that an examination has been successful can be achieved with oblique synthetic mammograms at an acquisition workstation. Finally, it can be possible for a better alignment with prior mammograms to be achieved by choosing the most suitable angular direction to view the synthetic mammogram when that angle is oblique from a central acquisition direction.

Of course, it will be understood that in a special case, the processed 3D volume data representing the data need not be the entire volume of the imaged target.

As will be described, the synthetic mammograms are computed such that artifacts arising from the limited angular range of the tomosynthesis acquisition geometry are largely suppressed, especially when forward-projecting in a direction other than the central acquisition direction where such artifacts are naturally the least prominent.

During the following description, the term "prior mammogram" is used to denote a 2D mammogram resulting from a previous mammography scan. Such a 2D mammogram may be the output of a digital mammography scanner, or may be a conventional X-ray film based mammogram which has been captured using a digital scanner.

During the following description, the term "processed 3D volume data" may be defined as a set of voxels characterizing a target in three dimensions. The processing occurs because of a need to generate the 3D volume data from a plurality of 2D X-ray images taken through a target, at a corresponding plurality of source positions. Any processing algorithm known in the art suitable for reconstructing a 3D volume from the 2D X-ray images may be applied.

During the following description, the term "acquisition direction" may be defined as the direction defined by a line projecting from an X-ray source at a current X-ray detector position, proceeding through a target location, and intersecting an X-ray detector element at a current detection position. Of course, in some embodiments the X-ray source and detector may move around an isocentre in unison, in which case the acquisition direction will form a perpendicular intersection with the X-ray detector. In other embodiments, the X-ray detector may not track the X-ray source position.

During the following description, the term "central acquisition direction" may be defined, closely related to the term "acquisition direction". A plurality of different source positions will define an acquisition trajectory between the source positions. The line passing through the central source position on this trajectory, the target, and intersecting the centre of the detector may be considered to be the central acquisition direction. In most cases, the central acquisition direction will correspond to the direction which is perpendicular to the center of the slices of the reconstructed 3D volume.

During the following description, the term "oblique" may be defined as not parallel to, and not perpendicular to a line or a plane.

During the following description, the term "forward projection" may be defined as the process of reconstructing, using a processing means, a 2D image from a set of 3D voxels. Conceptually, a virtual source position projects an arbitrary number of rays through a 3D volume. A virtual detector on the other side of the 3D volume receives each arbitrary ray. The intensity of each ray is modulated according to a combination of voxel values along the path of each ray (which may represent, for example, tissue density). Each pixel in the 2D image may be linked to each ray value to form the 2D image. It will be understood that other reconstruction/projection approaches are available.

Therefore, the forward projection is designed such that diagnostically relevant information is largely retained. The corresponding 2D views obtained in this manner for each direction of forward projection are referred to synthetic mammograms.

During the following description, the term "set" may be defined as containing one or more.

In this description, the term "slab" may be defined as a subset of a volume. The slice may have parallel sides. Alternatively, the slab may be wedge-shaped.

In this description, the term "slab projections" may be defined as forward projections through a slab of a processed 3D volume, rather than through the entire 3D volume. Images derived in this way would contain information about the density of material inside the slab, rather than the entire 3D volume.

These and other aspects of the invention will become apparent from, and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
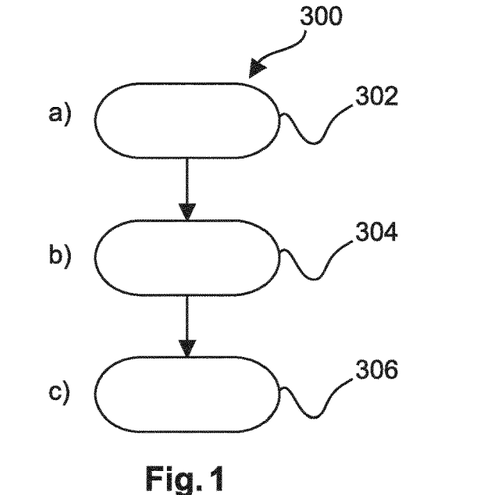
FIG. 1 schematically illustrates basic method steps of a method for displaying medical images acquired from a target using tomosynthesis.

FIG. 1 shows a method 300 for displaying medical images acquired from a target using tomosynthesis. The method comprises the following steps: In a first step 302, processed 3D volume data representing a target, computed from a plurality of X-ray images through the target acquired along a plurality of acquisition directions is provided. In a second step 304, a first set of forward projections is computed in one or more projection directions through the target as represented by the processed 3D volume data, wherein at least one of the projection directions is oblique relative to a central acquisition plane. In a third step 306, the first set of forward projections is displayed as a corresponding set of synthetic mammograms.

The first step 302 is referred to as step a), the second step 304 is referred to as step b), and the third step 306 is referred to as step c).

According to the invention, the viewing of images from the 3D volume data, for example, synthetic mammograms in oblique directions, enables the presentation of the 3D tomosynthesis data in one or more of a set of synthetic 2D mammograms as a first overview of the patient data. This aids a radiologist by allowing them to more effectively search the 3D volume for abnormalities. In addition, the use of a virtual projection direction, which can be oblique, enables a much greater range of potential views of the 3D volume data.

Figure 2:
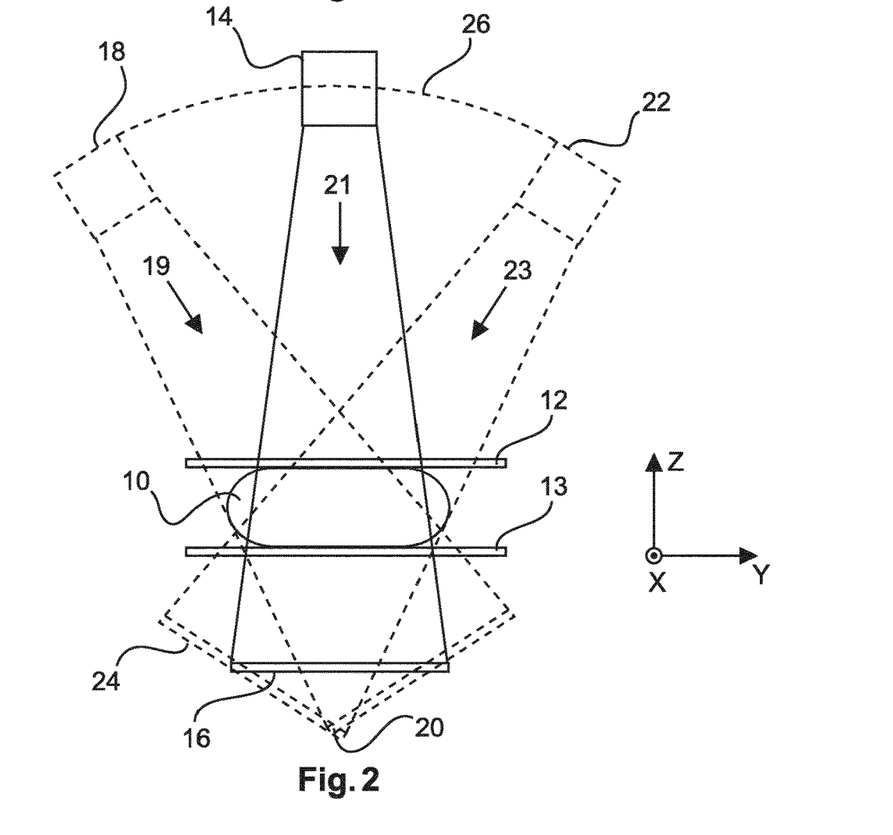
FIG. 2 illustrates an image acquisition process.

With reference to FIG. 2, the basic description of the acquisition of images by tomosynthesis is explained. Tomosynthesis is one exemplary method by which 3D volume data may be acquired. It will be understood, though, that the invention may be applied to 3D volume data acquired from other X-ray imaging systems such as CT or C-Arm systems.

FIG. 2 shows a target 10, for example a breast, held between two compression plates 12 and 13. Arranged above this arrangement is an X-ray source 14 and directly below the target and the compression plates is an X-ray detector 16. Thus, the X-ray source is configured to illuminate the target. The intensity of the X-rays after passing through the target can be detected by the X-ray detector 16. FIG. 2 also shows, with dotted lines, two further X-ray source and X-ray detector positions. The X-ray source 18 is rotated or translated counterclockwise with respect to the X-ray source position 14. The X-ray detector position 20 has rotated in correspondence, to match this new position. In addition, X-ray source at position 22 has rotated clockwise with respect to the original X-ray source position 14 and X-ray detector position 24 has changed commensurately.

Of course, many other X-ray source and X-ray detector translation regimes may be applied during image acquisition, such as a horizontal translation. Such variations do not affect the working of the invention.

Thus, it is possible to image sections of the target 10, or the entire target, from many different angles. The X-ray source 14 may move to alternative positions, such as shown by the X-ray sources at positions 18 or 22 along the trajectory 26. It will be appreciated that the X-ray source 14 may stop at any point on this trajectory 26 to image the target. Of course, the trajectory need not be a straight line or an arc but is simply defined to illustrate that X-ray acquisition may take place from a number of different angles. Thus, the target 10 can be imaged from a plurality of different X-ray source positions. It will also be seen that in an example, the X-ray detector 16 need not move with the X-ray source 14 into the positions, such as shown by the detectors 20 or 24, but remain stationary at position 16. It will also be appreciated that other types of X-ray equipment allow substantially the same principle of the acquisition of image data through a target. For example, a CT scanner or a C-arm X-ray system can acquire target data, in an embodiment. Thus, during a standard tomosynthesis acquisition sequence, an X-ray source may begin at the position 18 to illuminate the target onto detected position 20, then move along the trajectory 26 to illuminate the target from a number of different positions.

The axes shown in FIG. 2 illustrate that the vertical direction is, for the purposes of this description, described in the z-direction. The scanning direction of an example X-ray source scanning trajectory occurs in the y-direction. The x-axis is orthogonal to the plane of drawing.

Figure 3:
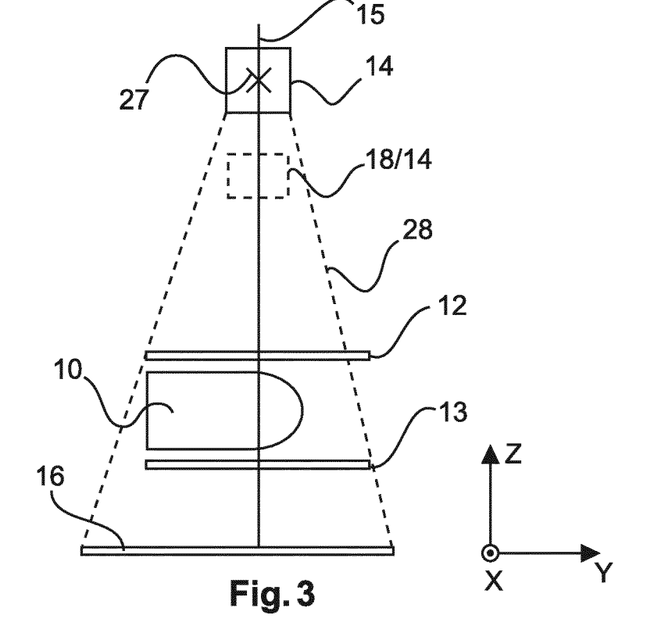
FIG. 3 illustrates an image acquisition arrangement.

FIG. 3 shows a side view of an example X-ray tomosynthesis image acquisition arrangement of FIG. 2, as shown by the adjusted axes. Thus, it can be seen that a ray path 28 emitted from the X-ray source 14 penetrates through the target 10, which is held in place by compression paddles 12 and 13. The ray which has illuminated the target 10 is incident on the X-ray detector 16. A cross 27 illustrates the centre of an exemplary X-ray source acquisition axis. The dotted square 18, 14 illustrates, as viewed in the direction of travel of the X-ray source, terminal positions of the X-ray source as it moves to either side of the axis.

A central acquisition position is indicated with line 15 in FIG. 2.

As is known in the art, tomosynthesis is understood to mean the generation of a set of slice images from a summation of a set of shifted projection images acquired at different orientations of an X-ray source, as made possible with the arrangements illustrated in FIG. 2 and FIG. 3. This so-called shift-and-add approach reconstructs image objects within the target 10, which will appear at different heights z above the detector location. Therefore, as the X-ray source moves, the objects will experience different degrees of parallax.

Hence, objects occurring at different heights in the target 10 will be projected onto the detector at positions dependent on the relative heights of the objects in the target. If the X-ray source and detector move in synchrony, the magnification of objects depends only on their height z above the detector and not on the locations of the X-ray source or detector within these two planes.

Therefore, it is possible to shift and add images acquired during this movement such that structures in the same plane are all made to line up exactly, and thus be in focus. Structures in other planes are distributed over the entire image and appear blurred. Although the illustrations in FIG. 2 and FIG. 3 concern tomosynthesis using an isocentric movement, in which the X-ray source and the detector move in an arc about some centre of motion, this description is also valid for the conventional tomosynthesis case, where the detector and X-ray source move in a parallel plane, as will be appreciated by the skilled person.

As is known in the art, once a plurality of sets of data acquired at different projection angles have been acquired, a processing operation is required to construct a 3D volume representing the target. Thus, pixels in the plurality of 2D detected images are processed to form voxels in the processed 3D volume data. A variation in voxel intensity can represent a quality of the target, such as a density. The 3D volume data thus processed represents the target. Many such reconstruction algorithms are known to the person skilled in the art and will not be described further here.

To reconstruct a 2D synthetic mammogram from the processed 3D volume data representing the target, a forward projection step through the 3D volume, carried out virtually, is required. The forward projection may be thought of as providing, from a position on the acquisition trajectory, a large plurality of virtual rays through the processed 3D volume data towards a virtual detector plane on the opposite side of the target (represented by the virtual 3D volume). For each of the plurality of virtual rays, the 3D voxels of the processed 3D volume data in-between the virtual source position and the virtual detector plane are added up. Voxels indicative of normal tissue may have a particular attenuation. Furthermore, voxels representing abnormal tissue may have a different attenuation. Thus, it will be seen that the calculation of a large plurality of ray values from a virtual source position on the central acquisition trajectory towards a virtual detector enable a 2D synthetic mammogram to be reconstructed from the 3D volume data representing the target.

It is an essential aspect of this invention that a first set of forward projections is computed in one or more projection directions through the target 10 as represented by the processed 3D volume data, wherein at least one of the projection directions is oblique relative to a central acquisition plane.

Of course, it will be understood that in one case, a set may contain a single element. Therefore, in an example, only one forward projection may be calculated, which has an oblique direction relative to a central acquisition direction.

If the set contains more than one element, for example two, three, four, five, or more, the succession of 2D images through the target may be thought of as a sequence. In an embodiment, they may be suitable for display as a dynamic video.

Figure 4:
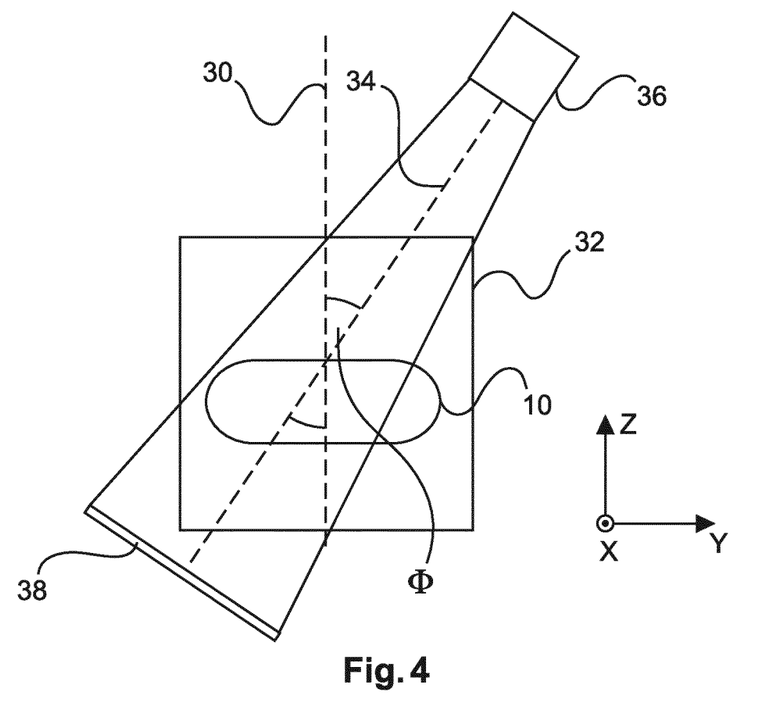
FIG. 4 illustrates a still further example of the image acquisition.

FIG. 4 shows the computation of a forward projection at an angle oblique to a central acquisition direction 30. In FIG. 4, feature 40 represents processed 3D volume data representing the target 10. The processed 3D volume data exists within a coordinate system 32 defined by a box. It will be appreciated that this coordinate system is not essential to the definition of the invention. Any coordinate system could be used, provided at least one forward projection is oblique relative to a central acquisition direction. This coordinate system may be Cartesian or a skewed (conic) coordinate system or another, more general representation.

In FIG. 4, the forward projection through the processed 3D volume data 40 occurs from a virtual forward projection position 36. The forward projection may consist of a large plurality of rays. One such ray is shown at 34. Having passed through the processed 3D volume data, the magnitude of each ray on a virtual detection surface 38 is calculated so that a 2D synthetic mammogram can be provided. The line 30 represents the central acquisition direction which may be considered to be aligned with the acquisition trajectory of the X-ray sources in FIGS. 2 and 3. In the conventional generation of 2D synthetic mammograms, the forward projections through the processed 3D volume data representing a target occur along this axis.

According to the invention, a first set of forward projections may be computed from the position 36. The position 36 is oblique to the central acquisition direction. This is shown by the angle, $\Phi$, which indicates that the virtual forward projection through the processed 3D volume data is oblique to the acquisition direction 30. Thus, a 2D synthetic mammogram, which is oblique to the original acquisition direction, may be computed. In general, this can be extended to a direction rotated out of the drawing plane (y-z plane).

A set may contain one projection or it may contain a plurality of projections. Because a forward projection may be calculated at an angle oblique to a central acquisition direction, the acquired tomosynthesis image or set of images is not restricted only to the angles of the X-ray source during the tomosynthesis projection sequence.

Figure 5A:
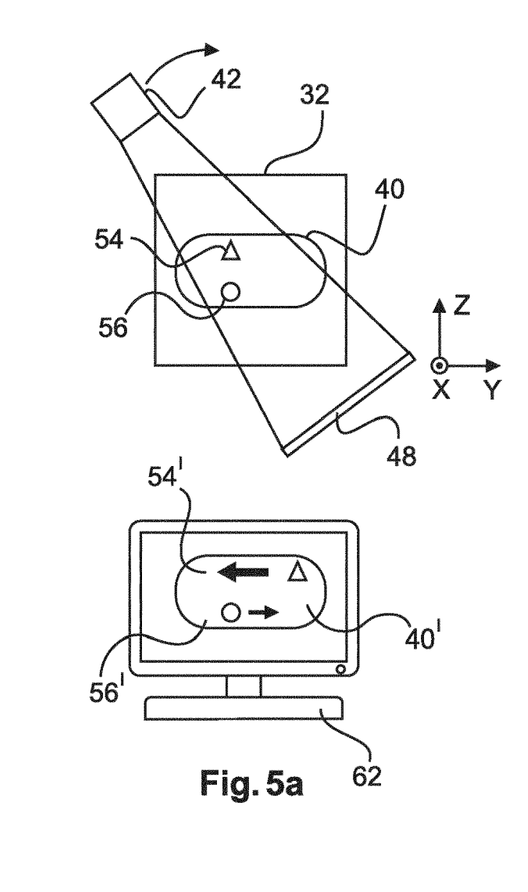
FIG. 5 illustrates examples resulting from the application of the method.
Figure 5B:
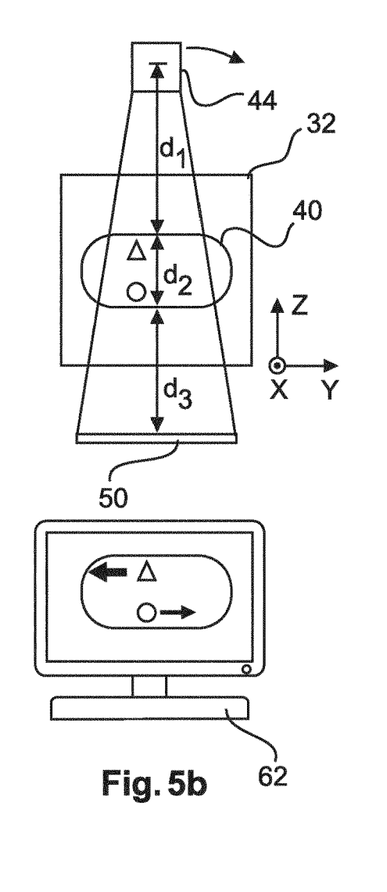
Figure 5C:
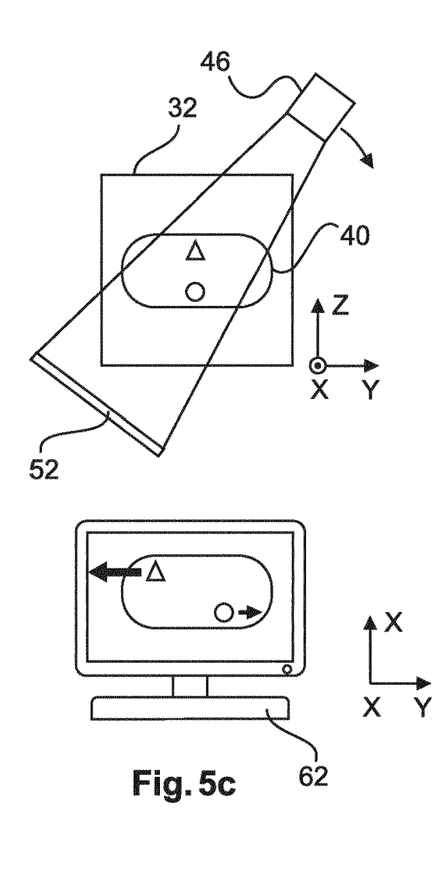

FIG. 5 illustrates the successive display by forward projection of two abnormalities in a processed 3D image volume originating from a target. Therefore, a display screen 62 displays a 2D synthetic mammogram obtained from the forward projection through the processed 3D volume data. Such 2D synthetic mammograms may, in certain cases, be more acceptable to medical personnel, because merely displaying slices of the 3D volume means that it is a laborious task to search through slices of the volume 40. Instead, according to the method outlined above using oblique forward projection angles through the target 10, medical personnel can search for abnormalities in the entire breast volume from different forward projection angles, including oblique forward projection angles, without having to consider individual slice values. This allows the medical personnel to quickly and easily achieve a quick overview of a specific case.

FIG. 5 illustrates an example of the creation of a synthetic mammogram from 3D processed volume data 40 from three different virtual source positions 42, 44, 46. It is to be understood that as part of a dynamic display process, the virtual source may pan around the processed 3D volume data 40.

In FIG. 5, processed 3D volume data 40 is provided, originating from a target 10 containing two abnormalities. The processed 3D volume data therefore contains a representation in 3D of a first abnormality 54 and a second abnormality 56.

In each of the three instances, the position of the abnormalities in the target does not change. Although in the top row of FIGS. 5a to 5c, the abnormalities appear to be on top of each other (at the same x-axis coordinate), it is to be understood that, in fact, the abnormalities are displaced in the x-direction (into the page). Therefore, the abnormalities are disposed side-by-side in the 2D synthetic mammogram images as seen in the bottom row of FIGS. 5a to 5c. This is also denoted by the change of orientation of the reference axes shown at the right of the FIG. 5, between the top and the bottom rows.

The top row of FIG. 5 shows the processed 3D volume data 40 surrounded by the exemplary fixed coordinate system 32, which is related to the data format of the processed 3D volume data, and which is not essential for the definition of the invention.

In a) of FIG. 5, a virtual forward projection position is shown initially at position 42 with a virtual image detection position shown at position 48.

In b) of FIG. 5, the virtual forward projection position has moved to position 44 and a commensurate alteration of the virtual forward projection detection position 50 has been made.

Finally, in c) of FIG. 5, the virtual forward projection position 46 is shown along with the virtual detection position 52. Thus, a set of three forward projections is shown in FIG. 5.

At least one of the projection directions shown in FIG. 5 by position 42, position 44 or position 46 is oblique, relative to a central acquisition direction of the processed 3D volume data originally acquired in an X-ray scanning apparatus.

A first distance $d_1$ represents the position between the virtual forward projection position and the first abnormality 54 in the volume 40.

A second distance $d_2$ illustrates the distance separating the first abnormality 54 and the second abnormality 56 in the processed 3D volume data 40.

A third distance $d_3$ represents the distance between the second abnormality 56 and the virtual detector's surface.

The bottom row of FIG. 5 illustrates a display resulting from a forward projection from the associated virtual forward projection position in the first row.

As will be seen in FIG. 5, a)-c), as the virtual forward projection position 42, 44, 46 pans over the processed 3D volume data 40, there is a commensurate change in the relative location of the images of the first and second abnormalities 54' and 56' projected onto the virtual detector 48, the output which is here shown on screen 62.

The second distance $d_2$ between the virtual detector surface and the second abnormality 56 is smaller than the distance $d_2+d_1$ between the virtual detector surface and the first abnormality 54. Therefore, it will be seen that as the virtual forward projection position moves over the processed 3D image data 40, the rate of change of the positions of the images of abnormalities 54' and 56' is different.

As shown by the larger arrow, an image 54' of the first abnormality 54 moves quickly relative to the change in virtual forward projection position. An image 56' of the second abnormality 56 changes position more slowly in the target volume relative to the image of the first abnormality 54' as the virtual forward projection position is moved from left to right.

As will be seen, the images of the first and second abnormalities move in opposite directions, thus crossing over when the virtual projection position 44 is located perpendicular to the central acquisition direction.

At least one forward projection may be taken obliquely relative to a central acquisition direction. Therefore, the relative depth position of different abnormalities inside the processed 3D volume data 40 may more easily be observed by a medical practitioner. This may aid medical personnel in the identification of abnormalities inside the target 10. Additionally, a much greater range of potential views of the processed 3D volume data is possible when oblique views are enabled.

Therefore, the plurality of X-ray images is acquired in a spatial acquisition sequence comprising discrete positions of an X-ray source and an X-ray detector on an acquisition path, wherein an acquisition direction of the sequence between the X-ray source and the X-ray detector is used in the acquisition. At least one synthetic image (synthetic mammogram) can be computed in oblique directions relative to the acquisition sequence.

When computing forward projections through the processed 3D tomosynthesis volume, methods of improved resolution may be required. Conventionally, the forward projection can be implemented as an averaging of all slices, or using the maximum intensity projection (MIP). However, these approaches are known to suffer from a loss of spatial resolution such that the sharpness of the 3D volume is not retained. In addition, some structures such as lesions visible in the calculated image may be hidden by other, brighter, objects.

Therefore, according to an example, a method is provided to display medical images acquired from a target represented by a 3D volume, wherein a step of computing a first set of forward projections in one or more projection directions through the target as represented by the processed 3D volume data includes, for each of the first set of forward projections, enhancing regions of the processed 3D volume using, for example, an edge retaining algorithm. By using oblique forward projections through the 3D volume, a loss of definition may be observed owing to interpolation. Enhancement of the edges in the 3D volume prior or in the forward projection step may improve this effect.

Therefore, voxels in the processed 3D volume data with high information content, such as a high edge measure, may be emphasized in the synthetic mammogram. This is important due to the highly anisotropic point spread function in tomosynthesis images. The practical impact of this effect is that most structures are sharply represented in only one or two slices of the volume, but blur towards the adjacent slices. This blurring causes artifacts, which would, conventionally, also be visible in the synthetic views, especially when not projecting along the central acquisition direction.

Therefore, a 3D weighting function (spatial filter, spatial high-pass filter) may be calculated for each processed 3D volume such that regions in slices with maximum sharpness have a high weight value. This can be achieved by applying a filter algorithm to the reconstructed volume that generates a high response at strong edges, from which the weighting function can be derived in a normalization step. Therefore, a reduced response to the artifacts, which may be blurred into the adjacent slices, may be obtained.

In practice, such an edge retaining function may be considered to involve providing an additional 3D "volume" corresponding to the original 3D volume. The additional volume contains voxels having a high value for structures representing the edge of a structure. When the forward projection process through the original processed 3D volume data is implemented, a ray is tracked through the processed 3D volume data representing the target. An analogous position in the additional 3D edge retaining volume is also tracked. Regions of the processed 3D volume data, upon which the ray is incident, and which are known to represent an edge, according to the edge weighting volume, are emphasized in the forward projection. Therefore, such an approach retains sharp structures and edges in an imaged volume, without blurring by averaging irrelevant slices not representing the target's structure.

The edge-retaining filter volume can be obtained, for instance, by applying the Sobel operator to the original processed 3D volume. The application of such an edge retaining algorithm enables a forward projection obtained obliquely through the processed 3D volume data relative to a central acquisition direction to have improved resolution.

In an example, the edge retaining algorithm can be implemented as follows: Let $e(r)$ be an edge measure, defined for every voxel position r within the 3D tomosynthesis volume $I(r)$. Such an edge measure can be obtained, for instance, by applying the Sobel operator as discussed above. The, let $w(r)=f[e(r)]$ be the local weights, where $f[.]$ is a function for shaping the weights.

The synthetic mammogram S can then be calculated as the weighted projection:

$$S = \frac{FP^d(w(r) \cdot I(r))}{FP^d(w(r))}$$

where $FP^d(.)$ is the forward projection operator along a selected direction d.

Figure 6:
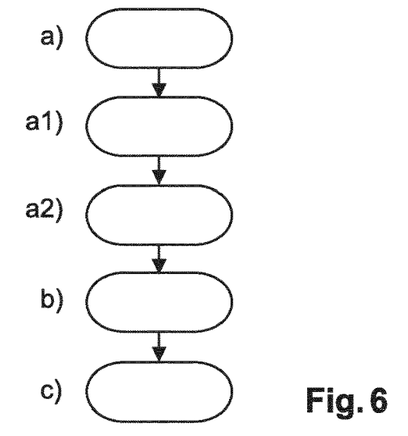
FIG. 6 illustrates schematically a further example of a method for displaying medical images acquired from a target using tomosynthesis.

According to a further embodiment of the invention, shown in FIG. 6, between the step of providing processed 3D volume data representing a target and the step of computing the set of forward projections, there are the further steps of a1) providing a prior mammogram image; and a2) computing an optimal forward projection angle through the 3D volume data which matches the projection angle of the prior mammogram image.

Additionally, in the step of displaying the first set of forward projections, the first set of synthetic mammograms is displayed beginning from the computed optimal forward projection angle through the 3D volume data.

The display of an oblique synthetic mammogram based on a prior mammogram image enables the most suitable angular direction in the forward projection step to be chosen, which may be oblique. In this way, a medical practitioner can very easily align previous mammogram examinations with an acquired processed 3D volume data.

Therefore, according to this embodiment, the radiologist selects a prior mammogram acquired by a prior imaging process such as by digital mammography, tomosynthesis or through a conventional mammogram, which has been digitized. This is used to begin an automatic procedure for displaying the synthetic mammogram in a direction which is optimally aligned with the selected prior mammogram. Of course, owing to unavoidable differences in the compression of the target between examinations, the calculated projection angle between the prior mammogram and the processed 3D volume data is very likely to be oblique.

Therefore, according to this embodiment, a 2D tomosynthesis image from processed 3D volume data may be displayed at the oblique angle that a prior mammogram image is subject to relative to processed 3D volume data acquired during a subsequent scan.

In an exemplary embodiment, the radiologist may select from a group of computed synthetic mammograms in different oblique views the one which is most similar to the prior mammograms.

In another embodiment, an optimal view angle is computed by maximizing a similarity measure between the prior mammogram and a computed synthetic mammogram with variable oblique view.

In an example, the prior mammogram is a prior synthetic mammogram.

In a further example, the prior mammogram image is from a digital mammography detector.

In a further example, the prior mammogram image is from a conventional mammography negative slide, which has been digitally scanned.

Figure 7:
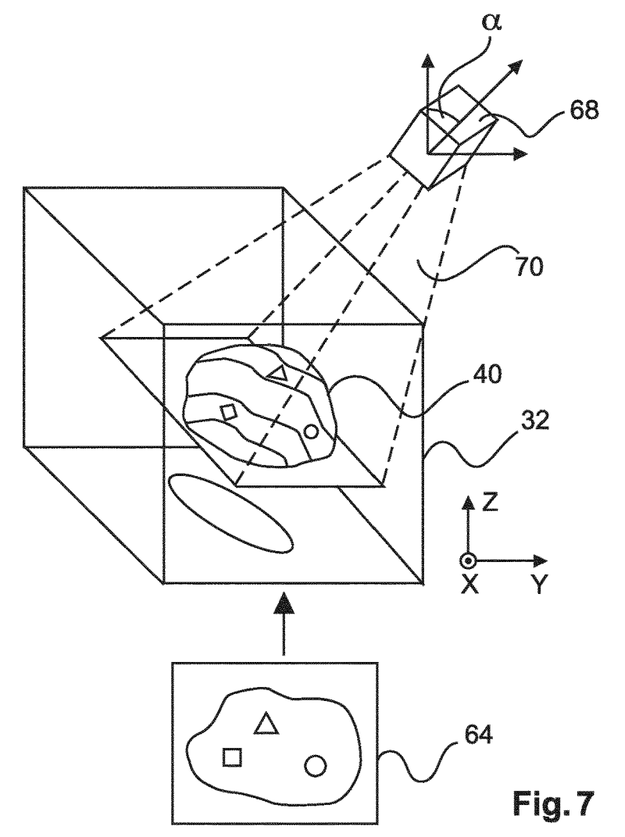
FIG. 7 illustrates a further example of an imaging arrangement.

FIG. 7 illustrates the provision of a synthetic mammogram according to this embodiment of the invention. In FIG. 7, a prior mammogram 64 acquired through any of the examples described previously may be provided. Also shown in FIG. 7 is processed 3D volume data 40 representing a target 10. This is contained within a coordinate system 32 and, as described previously, the definition of the coordinate system 32 is merely to aid understanding and is not essential to the definition of the invention.

In FIG. 7, the plane of the prior mammogram 64 is found according to the best match obtained with structures evident in the prior mammogram compared to structures evident inside a synthetic mammogram computed from the 3D volume data 40. It will be appreciated by the skilled reader that many search algorithms may be applied to enable the alignment of the 2D prior mammogram plane with the synthetic mammogram plane in the best oblique view through the 3D volume data which matches the plane of the prior mammogram 64.

In other words, the virtual source 68 is moved around the processed 3D volume data 40, in line with a (not shown) virtual detector surface "underneath" the processed 3D volume data. As the virtual source and virtual detector move around the volume, there will be a commensurate change in the computed synthetic mammogram related to the incidence of rays on the virtual detector surface, as discussed previously. This change can be compared to a 2D prior mammogram using 2D image correlation metrics known to those skilled in the art. A search space of virtual source/detector pair positions can be defined. For a set of virtual source/detector pair positions, when the 2D image correlation metric between the computed 2D mammogram and the 2D prior mammogram is maximized, it is known that the optimal virtual projection angle for that set of search positions through the 3D volume data has been found.

Once the optimal oblique view through the processed 3D volume data has been found, the coordinates defining it may be output. Such coordinates can be used to compute a virtual source position 68. In other words, lines tracking from the edge of the prior mammogram 64 towards the virtual source position 68, which encompass the processed 3D volume data 40, define a projection through the processed 3D volume data representing the position of the X-ray source used to acquire the prior mammogram 64. It will be appreciated by the skilled reader that a set comprising a single synthetic mammogram may be calculated.

Advantageously, this enables the comparison of changes in the target structure between two mammograms. Alternatively, this can be thought of as facilitating compatibility between obsolete and new imaging modalities.

In an alternative embodiment, a plurality of forward projections may be calculated beginning from the computed virtual forward projection 68. This enables a medical practitioner to follow the relative motion of abnormalities inside the target 40 starting from the last well-known position of the abnormalities.

According to a further embodiment of the invention, the step of computing an optimal forward projection angle through the 3D volume data, which matches the projection angle of the prior mammogram image, further comprises computing the optimal projection angle through the 3D volume data using a similarity measure.

Therefore, the chosen oblique viewing direction of the synthetic mammogram may be made closer to the viewing direction of the prior mammogram. This is advantageous, because a matching algorithm may not be able to provide an accurate determination of the position of the plane of the prior mammogram in the processed 3D volume data 40 without optimization. Therefore, the similarity measure may be iteratively maximized an arbitrary number of times until the best virtual source position for alignment with the prior mammogram has been obtained.

According to a further exemplary embodiment of the invention, a method for displaying medical images acquired from a target using, for example, tomosynthesis is provided, wherein between the step of computing the optimal projection angle through the 3D volume data using a similarity measure and the step of computing the first set of forward projections, there is a further step of applying an elastic registration algorithm to the processed 3D volume data to compensate for a modification in target shape.

Figure 8:
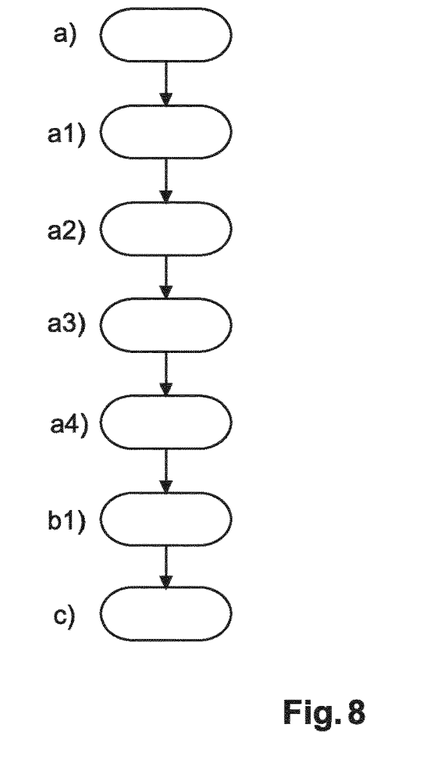
FIG. 8 illustrates an example of method steps for displaying medical images acquired from a target using tomosynthesis.

This embodiment is illustrated in FIG. 8.

Compression paddles may cause a deformation of the target, and thus the relative location of abnormalities inside the target. On multiple imaging acquisition occasions, the compression paddles will vary in position and will thus cause differing distortions in the target. This could cause a difficulty in identifying the location of abnormalities inside the target between different images. For example, it will be difficult to notice whether the differing location of a target between acquisitions was caused by growth of the abnormality, or by a difference in the arrangement of the compression paddles. This is relevant to this embodiment, because the compression paddles used to acquire the prior mammogram may differ from the position of the compression paddles used to acquire the processed 3D volume data representing the target. Applying an elastic registration either to the 3D volume or to the synthetic view or to the prior mammogram allows the alignment of the synthetic view and the prior mammogram is optimized. Elastic registration algorithms that could be applied to the processed 3D volume data are known in the art.

According to a further exemplary embodiment of the method, between the step of providing the processed 3D volume data and the step of computing the first set of forward projections, there is provided a step, a4), of providing eye-pair angle data of an observer. In addition, between step b) and step c) is a step, b1), of computing a second set of forward projections with an angular separation equal to the eye-pair angle of the observer. Finally, step c) comprises displaying the second set of forward projections as a corresponding second set of synthetic mammograms in parallel with the first set of synthetic mammograms using a technique to enable 3D viewing of the set of mammograms.

By calculating the eye-pair angle, for example of a radiologist, a 3D display of the target may be enabled. The 3D display may be achieved, for example, with 3D polarization glasses, or any other 3D display technique for volumes known in the art. Therefore, the radiologist will get a 3D impression of the target. Because the method enables the display of a synthetic mammogram at an oblique angle, the eye-pair angle may also result in a requirement to compute two oblique synthetic mammograms angularly separated by the typical viewing angle of the radiologist. These two views can then be displayed, for example, on interleaved rows of the monitor with orthogonal polarization such that the radiologist will get a 3D impression of the target 10.

Figure 9:
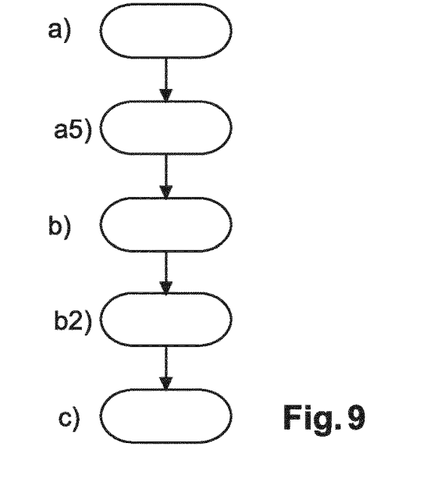
FIG. 9 illustrates a further example of a method.

FIG. 9 illustrates a further exemplary embodiment of the method. The step of providing processed 3D volume data further comprises between step a) and step b), a step, a5), of acquiring viewing path data from the user. Furthermore, between step b) and step c) is a step, b2), of computing the set of enhanced virtual forward projections of the target using forward projections determined using the viewing path data. Finally step c) further comprises displaying the set of synthetic mammograms as a cine-loop of synthetic mammogram images corresponding to the viewing path data. Thus, a cine-loop may be displayed, where at least one synthetic mammogram constituting the cine-loop may be from an oblique direction. Therefore, structures at different depths in the target will move at different relative speeds. This will be visible to the viewer. Therefore, the identification of abnormalities in the target may be easier to identify.

Figure 10:
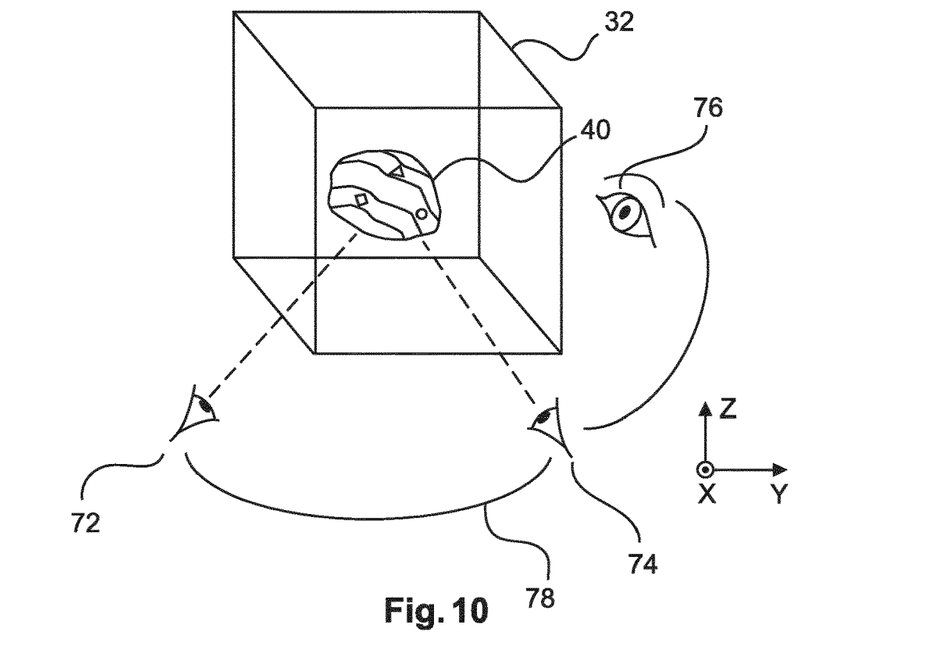
FIG. 10 illustrates the use of viewing path data.

FIG. 10 illustrates this embodiment. Viewing positions 72, 74 and 76 are shown along a trajectory 78. The processed 3D volume data 40 inside the coordinate reference 32 is also shown. The viewer may define the trajectory 78 so that sets of virtual forward projections are displayed at the positions 72, 74 and 76. Because the forward projections may be made from a position oblique, relative to a central acquisition plane of the 3D volume data representing a target 10, a much greater range of viewing positions of the trajectory 78 may be input by the user.

Figure 11:
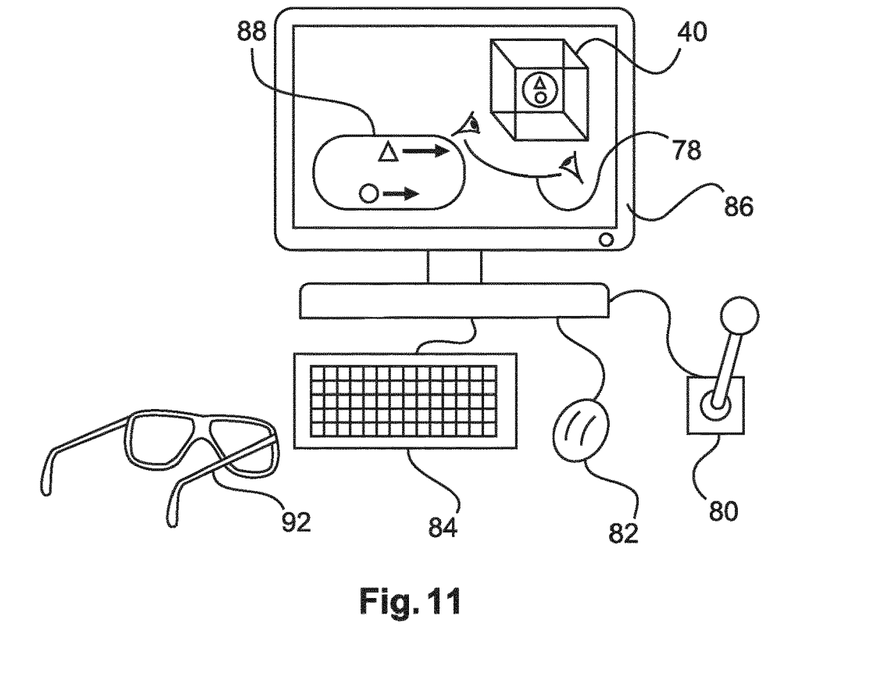
FIG. 11 illustrates various image viewing modalities.

The viewing path data is defined by the user using a control unit such as a joystick 80, a mouse 82, a keyboard 84 or any other form of input means. As shown in FIG. 11, the input means enable the viewing trajectory 78 to be input to a viewing system 86. Therefore, the relative motion of abnormalities inside a target 10 may be displayed as a synthetic mammogram 88 in the monitor 86 according to the user-selected trajectory 78. Optionally, a 3D representation of the target 10 may also be shown 90 inside the monitor 86. According to previous embodiments, a 3D display technique for example using polarization glasses 92 may also be used.

In an example, the viewing path data is defined in the cranio-caudal or the medio-lateral-oblique directions.

In an example, the user interface provides an animation of different synthetic views for improved spatial perception.

According to a further embodiment of the invention, the various embodiments described above may comprise:

between step a) and step b): providing a slab of the processed 3D volume data;

in step b): computing a first set of forward projections in one or more projection directions through the target as represented by the slab of the processed 3D volume data, wherein at least one of the projection directions is oblique relative to a central acquisition direction; and in step c): displaying the first set of forward projections as a corresponding first set of slab projections.

In this embodiment, the processed 3D data may be partitioned into slabs. In other words, a subset of the processed 3D data is used. The slab may be rectangular in shape, or in a wedge shape.

In an embodiment, a user may set the dimensions of the slab. In another embodiment, an automatic algorithm may be used to design a slab around features of interest, such as calcifications.

Once the slab dimensions have been identified, the extraneous processed 3D data may be removed, leaving only the slab. A forward projection step may then be performed through the slab, as described previously. In this case, the forward-projected image formed on the virtual detector as a result of the projection through the slab will exclude data not in the slab, which may serve only to blur the image or detract from interesting features.

The edge emphasis algorithm described previously may also be applied in this embodiment. Furthermore, it will be appreciated by the person skilled in the art that the forward slab projection can be performed at an angle oblique to the central acquisition direction. Therefore, the same technical effects as described above are apparent, albeit using a subset of the 3D volume. Structures at different depths in the slab may be observed tracking around the 2D image at different speeds, thus aiding diagnosis.

An advantage of this lies in the fact that sections of the volume with interesting features, such as lesions, may be singled-out for further investigation by medical personnel. The sections of the processed 3D data above and below the slab would otherwise detract from the image during the forward-projection step.

In an example, viewing the volume by adjusting the slab position and/or orientation may replace the conventional slice-by-slice viewing.

In an example, the oblique viewing process described above also resolves the problem of identifying overlaid structures (e.g. two distinct lesions on top of each other that obscure each other in the central forward projection). The viewing of overlaid structures is possible in the interactive mode, or alternatively as a part of automatically finding an optimal projection angle, such that the two obscured lesions appear next to each other in the synthetic view. Thus, in this example, to find the optimal viewing angle of 3D volume data containing several lesions, an algorithm causes a virtual source and detector pair to pan around the processed 3D volume data as shown in FIG. 7. In this case, there is be no requirement to provide a 2D prior mammogram. Instead, an image region recognition algorithm monitors the position, growth, shrinkage, or change in shape of lesion-defining areas on a dynamic 2D synthetic mammogram updated as the virtual source/detector pair panned around the processed 3D volume. An algorithm monitors the divergence of the image into two or more lesions. An optimization process can continue to search for the forward projection angle which displayed the multiple lesions with the greatest possible separation, rather than with the lesions obscuring each other. Algorithms that are designed to identify the divergence of one 2D area into two or more areas are known to those skilled in the art.

Figure 12:
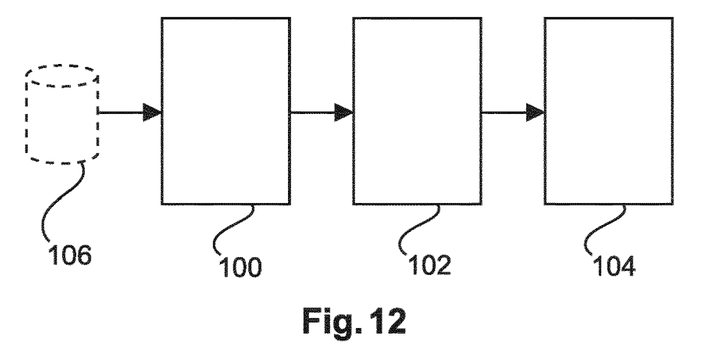
FIG. 12 illustrates a device for displaying medical images acquired from a target using tomosynthesis.

It will be appreciated that it would be advantageous to medical personnel to, be able easily to begin an examination seeing a 2D mammogram with possibly distinct separation of multiple lesions, rather than having to search for them individually. According to the invention, a device for displaying medical images acquired from a target using tomosynthesis is provided. The device comprises an interface unit 100, a processing unit 102 and a display unit 104. The interface unit 100 is configured to provide a processed 3D volume data representing a target computed from a plurality of X-ray images through the target 10 acquired along a plurality of acquisition directions 19, 21, 23. Furthermore, the processing unit 102, configured to compute a first set of forward projections in one or more projection directions through the target as represented by the processed 3D volume data, where at least one of the projection directions is oblique relative to a central acquisition direction. The display unit 104 is configured to display the first set of forward projections as a corresponding first set of synthetic mammograms.

An example of the device according to the invention is shown in FIG. 12. The processed 3D volume data representing the target may be provided according to an example, input to the system from a storage system 106 shown in dotted lines in FIG. 12. Alternatively, the 3D volume data may be acquired from an X-ray tomosynthesis device, a C-arm system, a CT system, or any other system of providing X-ray data such as a PACS system.

Figure 13:
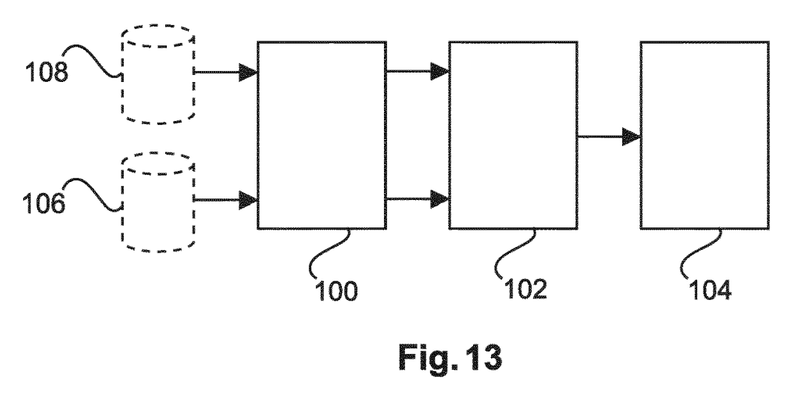
FIG. 13 illustrates a further example of a medical imaging device.

According to an exemplary embodiment of the invention, as shown in FIG. 13, a device for displaying synthetic mammograms may be provided, where for each of the first set of forward projections, regions of the processed 3D volume with maximum sharpness are emphasized using an edge retaining algorithm.

According to a further exemplary embodiment of the invention, a device is provided, where the interface unit 100 is configured additionally to input a prior mammogram imaging 108. The processing unit 102 is configured to compute an optimal forward projection angle through the 3D volume data which matches a projection angle of the prior mammogram image. The display unit 104 is configured to display the first set of synthetic mammograms beginning from the computed optimal forward projection angle through the 3D volume data.

Figure 14:
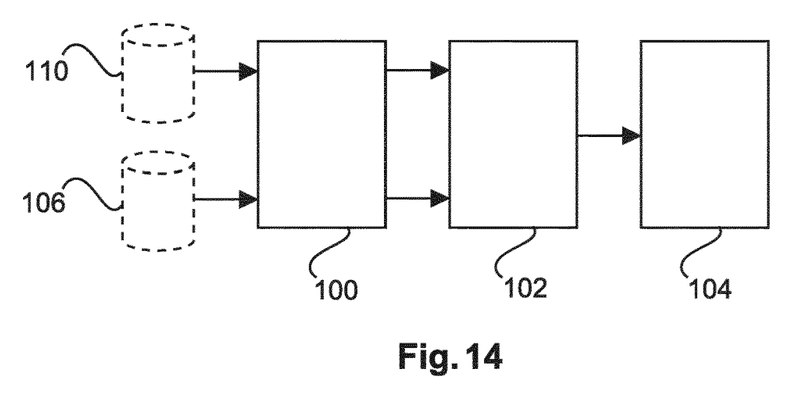
FIG. 14 illustrates a still further example of a medical imaging device.

According to a further exemplary embodiment of the invention as illustrated in FIG. 14, the interface unit 100 is further configured to provide eye-pair angle data of an observer to the processing unit. The processing unit 102 is configured to compute a second set of forward projections 110 with an angular separation equal to the eye-pair angle of an observer. Display unit 104 is further configured to display at least two synthetic mammograms using a technique to enable 3D viewing of the mammogram.

Figure 15:
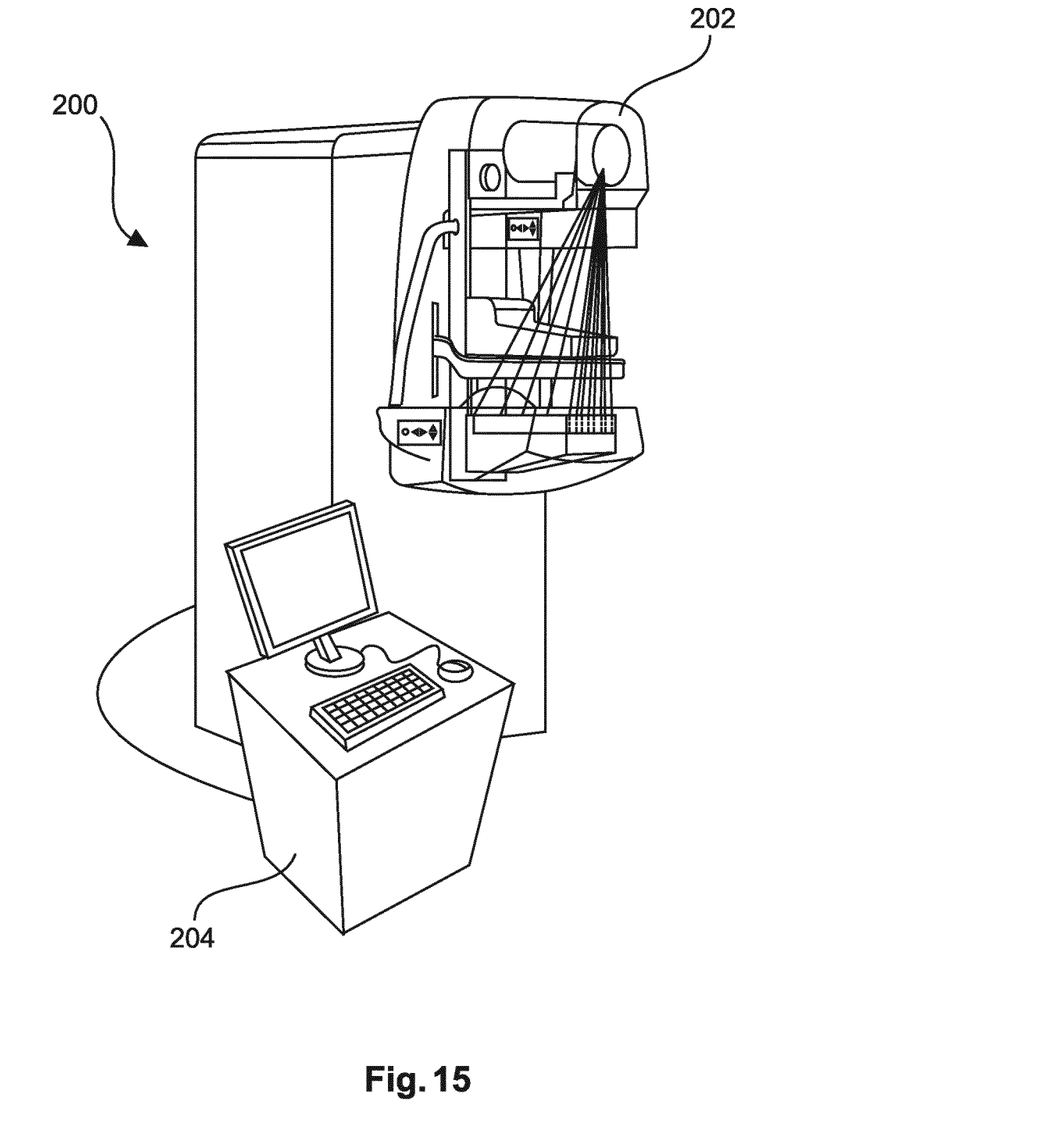
FIG. 15 illustrates an X-ray imaging system according to an example.

According to the invention, an X-ray imaging system 200 is provided that comprises an X-ray image acquisition arrangement 202, and a display arrangement 204. The display arrangement is provided as a device according to any of the previous examples. According to the invention, a computer program element for controlling a device for displaying medical images acquired from a target using tomosynthesis is provided which, when being executed by a processing unit, is adapted to perform the method steps of any of the embodiments described previously.

According to the invention, a computer-readable medium having stored the program of the previous example is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for displaying medical images acquired from a target using tomosynthesis, comprising:
    an interface unit configured to provide processed 3D volume data representing a target, the processed 3D volume data being computed from a plurality of X-ray images through the target acquired along a plurality of acquisition directions, wherein the interface unit is configured to input a prior mammogram image;
    a processing unit configured to compute a first set of forward projections in one or more projection directions through the processed 3D volume data, wherein at least one of the projection directions is oblique relative to a central acquisition direction, the processing unit being further configured to compute an optimal forward projection angle through the processed 3D volume data that matches the projection angle of the prior mammogram image; and
    a display unit configured to display the first set of forward projections as a corresponding first set of synthetic mammograms beginning from the computed optimal forward projection angle.

2. The device according to claim 1, wherein the interface unit is further configured to provide eye-pair angle data of an observer to the processing unit;
    wherein the processing unit is configured to compute a second set of forward projections with an angular separation equal to the eye-pair angle of an observer; and
    wherein the display unit is further configured to display at least two synthetic mammograms using a technique to enable 3D viewing of the mammogram.

3. A method for displaying medical images acquired from a target using tomosynthesis, comprising:
    providing processed 3D volume data representing a target, the processed 3D volume data being computed from a plurality of X-ray images through the target acquired along a plurality of acquisition directions;
    providing a prior mammogram image;
    computing an optimal forward projection angle through the processed 3D volume data that matches the projection angle of the prior mammogram image;
    computing a first set of forward projections in one or more projection directions through the processed 3D volume data, wherein at least one of the projection directions is oblique relative to a central acquisition plane; and
    displaying the first set of forward projections as a corresponding first set of synthetic mammograms beginning from the computed optimal forward projection angle.

4. The method according to claim 3, further comprising emphasizing, for each of the first set of forward projections, regions of the processed 3D volume with maximum sharpness using an edge retaining algorithm.

5. The method according to claim 3, further comprising computing the optimal projection angle through the processed 3D volume data using a similarity measure.

6. The method according to claim 3, further comprising:
    applying an elastic registration algorithm to the processed 3D volume to compensate for a modification in a target shape.

7. The method according to claim 3, further comprising:
    providing eye-pair angle data of an observer;
    computing a second set of forward projections with an angular separation equal to the eye-pair angle of an observer; and
    displaying the second set of forward projections as a corresponding second set of synthetic mammograms in parallel with the first set of synthetic mammograms, using a technique to enable 3D viewing of the set of mammograms.

8. The method according to claim 3, further comprising:
    acquiring viewing path data from the user;
    computing the set of enhanced virtual forward projections of the target using forward projections determined using the viewing path data; and
    displaying the set of synthetic mammograms as a cine-loop of synthetic mammogram images corresponding to the viewing path data.

9. The method according to claim 3, further comprising:
    providing a slab of the processed 3D volume data;
    computing a first set of forward projections in one or more projection directions through the target as represented by the slab of the processed 3D volume data, wherein at least one of the projection directions is oblique relative to a central acquisition direction; and
    displaying the first set of forward projections as a corresponding first set of slab projections.

10. An X-ray imaging system, comprising:
    an X-ray image acquisition arrangement; and
    a display arrangement;
    wherein the display arrangement is provided as a device according to claim 1.

11. A non-transitory computer-readable medium storing a computer program configured to control a device for displaying medical images acquired from a target using tomosynthesis, which, when being executed by a processor, is configured to perform the method of claim 3.

12. The device according to claim 1, wherein, for each of the first set of forward projections, regions of the processed 3D volume data with maximum sharpness are emphasized using an edge retaining algorithm.

* * * * *